US007020526B1

(12) United States Patent
Zhao

(10) Patent No.: US 7,020,526 B1
(45) Date of Patent: Mar. 28, 2006

(54) ELECTRONIC GASTRO-INTESTINAL STIMULATION DEVICE

(76) Inventor: Ruan Jin Zhao, 4440 Beauchamp Ct., Sarasota, FL (US) 34243

( * ) Notice: Subject to any disclaimer, the term of this patent is extended or adjusted under 35 U.S.C. 154(b) by 727 days.

(21) Appl. No.: 10/150,563

(22) Filed: May 16, 2002

(51) Int. Cl.
*A61N 1/36* (2006.01)
(52) U.S. Cl. .......................... 607/40; 607/133
(58) Field of Classification Search ............ 607/2, 607/40, 41, 133, 148
See application file for complete search history.

(56) References Cited

U.S. PATENT DOCUMENTS

| 3,411,507 | A | 11/1968 | Wingrove |
| 3,924,641 | A | 12/1975 | Weiss |
| 5,058,605 | A | 10/1991 | Slovak |
| 5,133,351 | A | 7/1992 | Masaki |
| 5,292,344 | A | 3/1994 | Douglas |
| 5,690,691 | A | 11/1997 | Chen |
| 5,957,951 | A | 9/1999 | Cazaux |
| 6,238,423 | B1 | 5/2001 | Bardy |
| 6,301,500 | B1 | 10/2001 | VanHerk |
| 6,338,347 | B1* | 1/2002 | Chung ........................ 600/9 |
| 6,885,896 | B1* | 4/2005 | Minogue et al. ............ 607/48 |

* cited by examiner

Primary Examiner—George R. Evanisko
(74) Attorney, Agent, or Firm—Charles J. Prescott

(57) ABSTRACT

A non-invasive percutaneously acting apparatus for relieving constipation or diarrhea and appropriately stimulating peristaltic movement in the human gastro-intestinal (GI) tract. The apparatus includes an annular or toroidal shaped hollow housing having a working surface on one side thereof. A multi-point electrode generally coextensive with the working surface includes a plurality of point electrodes each separately mounted in and preferably biasingly moveably extend outwardly from the working surface. A d.c. pulse generator selectively and sequentially connectable to the point electrodes whereby, when the working surface is positioned against or in close proximity to the skin over the GI tract, the point electrodes deliver electrical pulses percutaneously and sequentially moving from one point electrode to the next adjacent point electrode repeatedly around the working surface.

3 Claims, 3 Drawing Sheets

ELECTRONIC GASTRO-INTESTINAL STIMULATION DEVICE

BACKGROUND OF THE INVENTION

1. Scope of Invention

This invention relates generally to the treatment of gastrointestinal distress in the form of constipation and poor or sluggish peristaltic movement of material therethrough and diarrhea, and more particularly to a stimulating apparatus which introduces percutaneous pulsed electrical stimulation in circular fashion into and around the GI for constipation or diarrhea relief.

2. Prior Art

After leaving the stomach, the food and liquid material are directed through the various organs in the gastrointestinal (GI) tract of the human anatomy. Peristaltic movement of the GI in the form of timed moving contractions urges the food material through the various GI organs as nutrition is extracted resulting in the end product of fecal matter which is discharged from the anal area.

Various maladies as a result of the type of food ingested, the level of physical daily activity and disease all bear upon the efficiency and effectiveness of this peristaltic action in moving material through the GI. When various combinations of errors and weaknesses occur, constipation or diarrhea follows.

Various over-the-counter medications, as well as prescription medications, are available to assist in the stimulation or retardation of the GI tract so that the peristaltic action is with respect to the steady rhythmic flow through the GI tract. When these types of medications are inadequate, chronic constipation can occur leading to secondary maladies including significant discomfort, lethargy and other debilitating side effects of chronic constipation.

One very recent patented invention disclosed in U.S. Pat. No. 6,238,423 invented by Bardy teaches an anti-constipation apparatus including an implanted stimulus generator which supplies electrical stimuli to the muscles associated with specific target portions of a patient's GI or gut and extending all the way from the esophagus to the anus. One or more sensors may be provided to detect when one of the target portions is experiencing constipation.

Another similarly directed invention by Chen as disclosed in U.S. Pat. No. 5,690,691 teaches a portable or implantable gastric pacemaker with multiple electrodes positionable on the inner and outer surface of an organ in the GI tract individually programmed to deliver a phased electrical stimulation to pace peristaltic movement of material through the GI tract. Computer control is also provided to adjust and vary the stimulation parameters to achieve effective treatment and re-training of organs for natural pacing.

A more broadly useful electronic stimulation device is disclosed by Slovak in U.S. Pat. No. 5,058,605 disclosing a device for the controlled local non-invasive electro-stimulation of human and animal tissues. A pulse generator of adjustable frequency and amplitude provide the pulsed electrical current through two electrodes applied to the tissue.

Another portable device for acupuncture-type percutaneous treatment is disclosed in U.S. Pat. No. 5,957,951 by Cazaux. In this invention, a plurality of metallic contact blocks extend from the bottom of a casing. Each block acts as a terminal for discharging the pulsed output of a pulse generator positioned within the casing. The device is attachable around a body portion or torso of the user after which the device is allowed to operate for specific time limits and output intensities.

A somewhat older patented invention by Wingrove in U.S. Pat. No. 3,411,507 teaches a method of gastrointestinal stimulation with electrical pulses. This device envisions insertion of an elongated catheter with a distal end electrode into the stomach. The apparatus is intended to induce peristaltic waves into the antrum which cross the pylorus and are carried down to the duodenum.

Still another percutaneously placed electrical GI pacemaker is taught in U.S. Pat. No. 5,292,344 invented by Douglas. Electrical impulses are delivered to the inner lining of the GI tract in this invention while the system also senses the motor activity of the intestinal tract for feedback to the system. Other critical parameters of the GI are also monitored.

The following additional patented inventions each of which teach a more broadly applicable electro-stimulation apparatus for the human body are disclosed in the following U.S. patents:
U.S. Pat. No. 6,301,500 to Van Herk et al.
U.S. Pat. No. 5,133,351 to Masaki
U.S. Pat. No. 3,924,641 to Weiss

BRIEF SUMMARY OF THE INVENTION

This invention is directed to a non-invasive percutaneously acting apparatus for relieving constipation or diarrhea and appropriately stimulating peristaltic movement in the human gastrointestinal tract. The apparatus comprises an annular or toroidal shaped hollow housing having a working surface on one side thereof from which a multitude of point electrodes extend which make percutaneous contact with the skin surface over the GI tract. Pulsed electrical stimulation, which is phased or sequenced to move in a circular direction around the working surface and successively and sequentially through the point electrodes, is thereby introduced which both relieves constipation and stimulates peristaltic movement in the GI tract or in an opposite direction of phased stimulation, controls diarrhea.

It is therefore an object of this invention to provide a percutaneously acting electrical stimulator for the GI tract which relieves constipation and controls diarrhea.

It is yet another object of this invention to provide a portable, self-contained gastro-intestinal simulator which induces a circular series of electrical pulses into the GI tract for controlling either diarrhea or relieving constipation.

In accordance with these and other objects which will become apparent hereinafter, the instant invention will now be described with reference to the accompanying drawings.

DETAILED DESCRIPTION OF THE INVENTION

Figure 1:
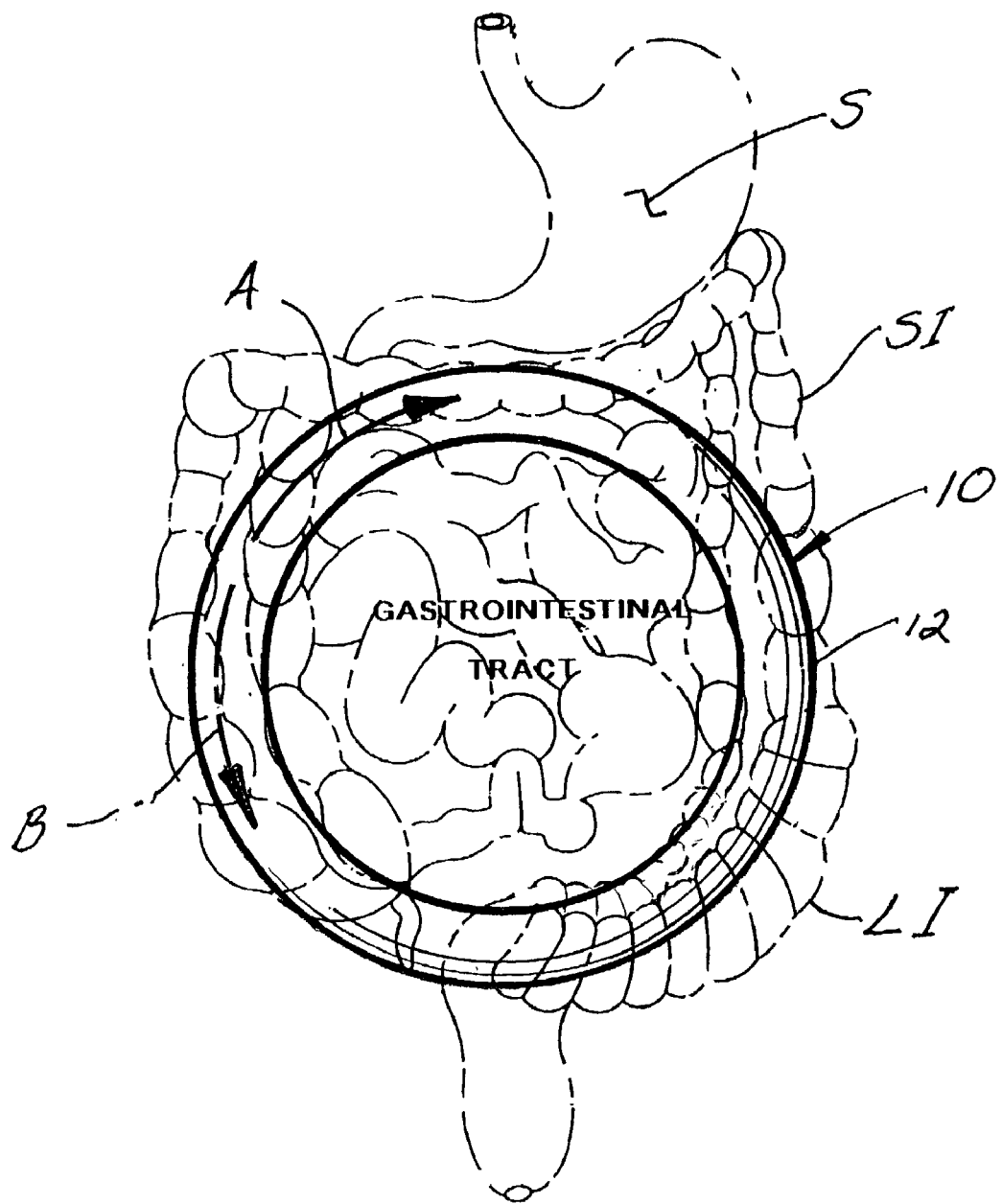
FIG. 1 is a front elevation view of the invention showing the relationship of GI tract in phantom with respect thereto.
Figure 2:
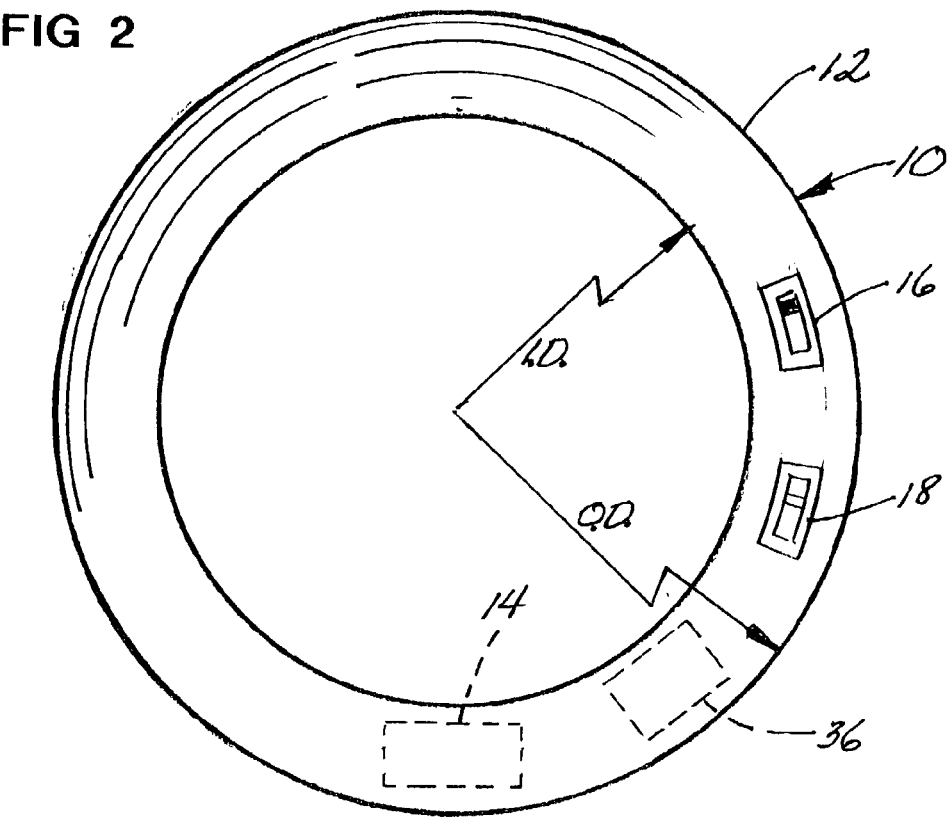
FIG. 2 is an enlarged more detailed view of the invention shown in FIG. 1.
Figure 3:
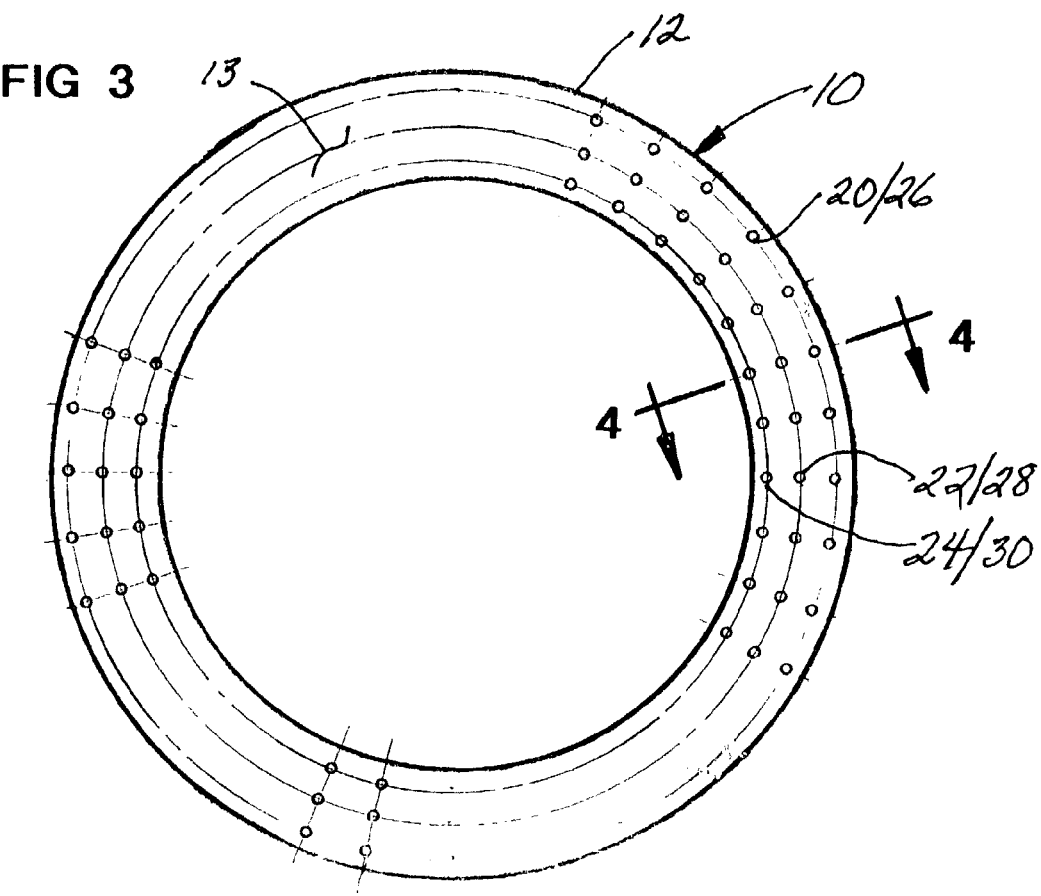
FIG. 3 is a rear elevation view of the invention of FIG. 1.

Referring now to the drawings and firstly to FIGS. 1 to 3, the invention is there shown generally at numeral 10 in the form of an annularly shaped apparatus having a housing 12 formed of thin wall plastic or other non-conductive material and defining an interior volume therewithin. Viewed another way, the housing 12 may be described as a modified toroidal three-dimensional configuration preferably having a substantially open central area and a generally flat ring-shaped working surface 13 which is operably positionable against the gastrointestinal (GI) tract as seen in FIG. 1. The overall size of the housing 12 is as shown in relation to the GI tract having an inside diameter of approximately 20 cm and an outside diameter of approximately 28 cm.

Within the hollow interior of the housing 12 is positioned an electrical storage battery 14 and a pulse generator 36 operably connected thereto. An on-off switch 16 with variable d.c. pulse magnitude control and a current direction control 18 are provided on the outer surface of the housing 12 as shown in FIG. 2.

As best seen in FIG. 3, an array of closely aligned point electrodes 26, 28 and 30 are each positioned within closely fitting holes 20, 22 and 24, respectively and which extend outwardly from the working surface 13 through those holes 20, 22 and 24, respectively. This arrangement of point electrodes 26, 28 and 30 extend in evenly spaced relationship of about 5° around the entire working surface 13 along three imaginary circular center lines also in radially spaced arrangement one to another.

Figure 4:
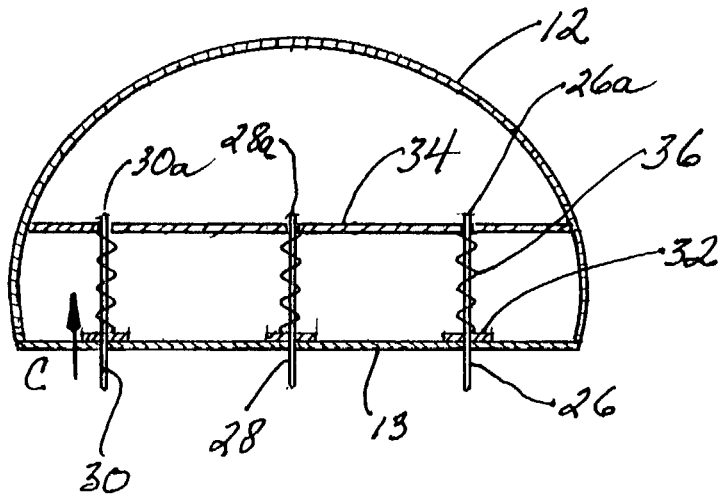
FIG. 4 is a section view in the direction of arrows 4—4 in FIG. 3.
Figure 5:
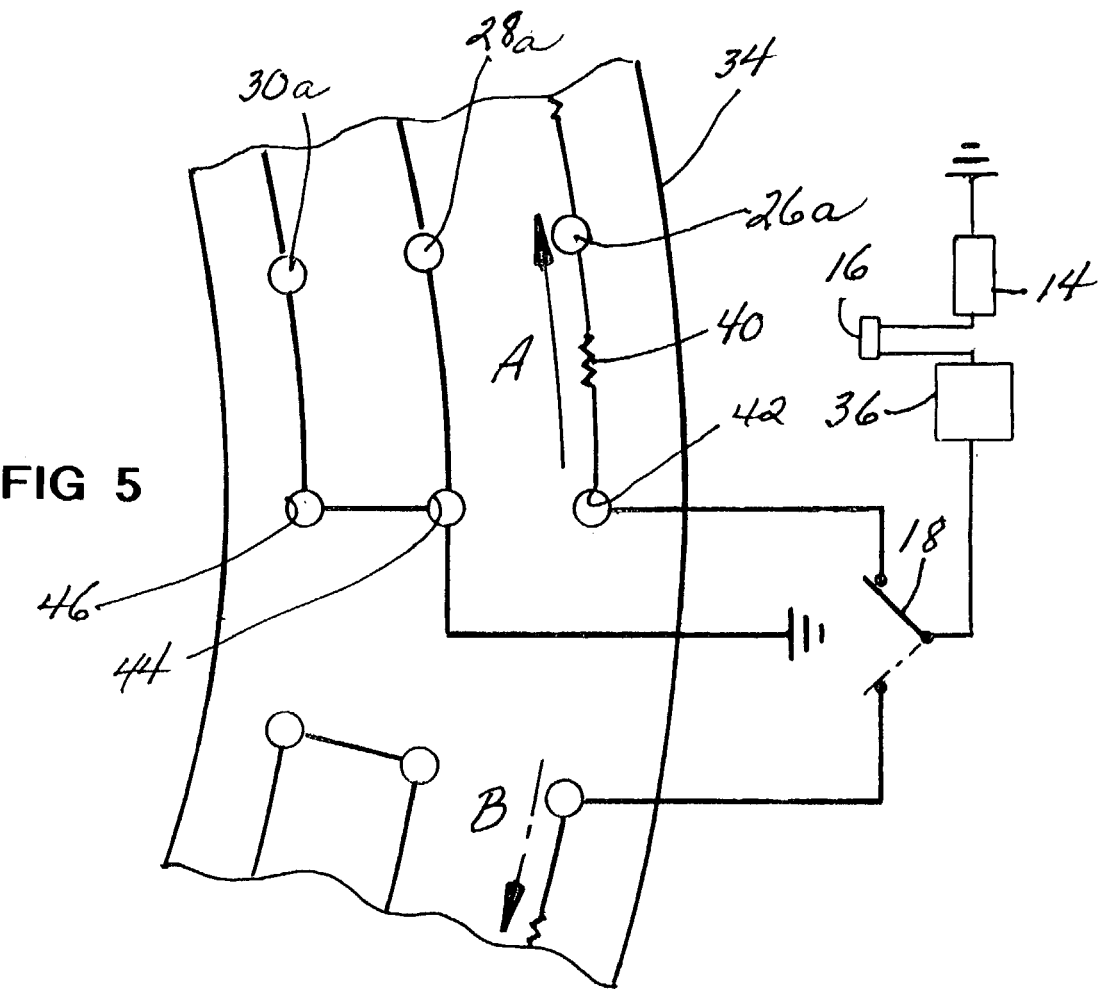
FIG. 5 is an enlarged front elevation plan view of a portion of the electronic circuit board/point electrode support of FIG. 4.

Referring additionally to FIGS. 4 and 5, each of the point electrodes 26, 28 and 30 forming a multi-point electrode include a disc-shaped stop shown typically at 32 which is rigidly attached to each of the elongated point electrodes 26, 28 and 30 adjacent the distal or exposed working end thereof as shown. The proximal or inner ends 26a, 28a and 30a extend upwardly through correspondingly aligned holes 42, 44 and 46, respectively, formed into a printed circuit board 34 which is also annularly or ring shaped and secured in the position shown in FIG. 4 within the housing 12. A compression spring shown typically at 36 acts between the lower surface of the circuit board 34 and the disc-shaped stop 32 so as to maintain each of the point electrodes 26, 28 and 30 in the extended position shown. However, upon slight pressure as when applied against the skin, each of the point electrodes 26, 28 and 30 will independently move in the direction of arrow C a corresponding amount in accordance with the pressure applied thereto.

As seen in FIG. 5, the circular array of point electrodes 28 and 30 are connected together to form a common ground contact of the skin with respect to the storage battery 12. The circular array of point electrodes 26, on the other hand, are connected to the positive output of the battery 14 through switch 16 and the pulse signal generator 36. Directional switch 18, when shown in the position in solid, will cause the current to flow in the direction of arrow A, also correspondingly shown in FIG. 1. Conversely, when the directional switch 18 is in the position shown in phantom, the pulsed current will flow in the direction of arrow B as also correspondingly seen in FIG. 1.

Delay resistors at 40 between each of the adjacent point contacts 26 provide the sequential delay in each pulsed signal delivered by the next adjacent point electrode 26. By this arrangement, an electric pulsed wave action is generated moving around the toroidal or annular configuration of the device 10 in either direction of arrow A or B as desired so as to appropriately stimulate the gastrointestinal tract to either enhance peristaltic movement through the GI tract or to inhibit it should diarrhea occur.

It should be noted that other arrangements of inducing positive pulsed electrical impulses into the point electrodes 26 or their equivalent are envisioned within the scope of this invention. Moreover, the ground or negative point electrodes 28 and 30 may also be replaced by a simple ground contact electrically connected to the skin of the patient or user in any arrangement in which a ground is established for return current.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

What is claimed is:

1. A non-invasive percutaneously acting apparatus for relieving constipation and stimulating peristaltic movement in the human gastro-intestinal (GI) tract comprising:
   a housing having an open central area generally defined by concentric outside and inside diameters of a generally toroidal-like configuration having a ring-shaped working surface on one side thereof;
   a multi-point electrode generally coextensive with said working surface and including a plurality of point electrodes each separately mounted at said working surface;
   said working surface and said electrodes adapted for positioning against substantially the perimeter area of the GI track along with said point electrodes;
   a d.c. pulse generator selectively and sequentially connectable to said point electrodes wherein, when said working surface is positioned against the skin over the GI tract, said pulse generator connects to said electrodes to deliver electrical pulses percutaneously and sequentially moving from one said point electrode to the next adjacent said point electrode repeatedly around said working surface for stimulating peristaltic movement and controlling either diarrhea or relieving constipation.

2. A non-invasive percutaneously acting apparatus for relieving constipation and stimulating peristaltic movement in the human gastrointestinal (GI) tract comprising:
   an annular-shaped housing having a hollow interior and a generally flat annular-shaped working surface on one side thereof;
   a multi-point electrode generally coextensive with said working surface and including a plurality of spring-biased point electrodes each separately mounted in and extending from and resiliently moveable orthogonally with respect to said working surface;
   a d.c. pulse generator and storage battery positioned and connected to each other in said hollow interior selectively and sequentially connectable to said point electrodes wherein, when said working surface is positioned against the skin over the GI tract, said pulse generator connects to said electrodes to deliver electrical pulses percutaneously and sequentially moving from one said point electrode to the next adjacent said point electrode repeatedly around said working surface.

3. A non-invasive percutaneously acting apparatus for relieving constipation and stimulating peristaltic movement in the human gastro-intestinal (GI) tract comprising:
   a housing having a substantially open central area defined by a generally annular shaped working surface adapted to substantially fit atop and against the perimeter of the GI tract;

a circuit board;

a multi-point electrode generally coextensive with said working surface and including a plurality of elongated spaced point electrodes each separately biasingly mounted in spaced hole pairs formed in the circuit board and extending outwardly from said working surface;

a d.c. pulse generator and storage battery connected to each other selectively and sequentially delivering d.c. pulses to said point electrodes wherein, when said working surface is positioned against or in dose proximity to the skin over the perimeter of the GI tract, said pulse generator connects to said electrodes to deliver electrical pulses percutaneously and sequentially moving from one said point electrode to the next adjacent said point electrode repeatedly around said working surface for stimulating peristaltic movement and controlling either diarrhea or relieving constipation.

* * * * *